(12) United States Patent
Di Ubaldi et al.

(10) Patent No.: US 10,842,983 B2
(45) Date of Patent: Nov. 24, 2020

(54) SYRINGE WITH ENTERAL CONNECTION FEATURE

(71) Applicant: Becton, Dickinson and Company, Franklin Lakes, NJ (US)

(72) Inventors: John Di Ubaldi, Jackson, NJ (US); Sambath Kumar Rajagopal, Tamil Nadu (IN); Thirumurugan Nagu, Ramanathapuram (IN); Gerald Bonczynski, Columbus, NE (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 722 days.

(21) Appl. No.: 15/286,655

(22) Filed: Oct. 6, 2016

(65) Prior Publication Data

US 2018/0099136 A1    Apr. 12, 2018

(51) Int. Cl.
*A61M 39/10* (2006.01)
*A61M 5/31* (2006.01)
*A61J 15/00* (2006.01)
*A61M 39/08* (2006.01)

(52) U.S. Cl.
CPC ...... *A61M 39/1011* (2013.01); *A61M 5/3134* (2013.01); *A61J 15/0076* (2015.05); *A61M 2039/085* (2013.01); *A61M 2039/1094* (2013.01); *A61M 2205/276* (2013.01)

(58) Field of Classification Search
CPC .. A61J 15/0076; A61J 15/0026; A61M 39/08; A61M 39/10; A61M 2039/1027; A61M 2039/1033; A61M 2039/1038; A61M 2039/1077; A61M 2205/27; A61M 2039/085; A61M 2039/1094; A61M 2205/276; A61M 39/1011; A61M 5/3134
USPC .......................................................... 604/241
See application file for complete search history.

(56) References Cited

U.S. PATENT DOCUMENTS

| 4,390,017 A | 6/1983 | Harrison et al. |
| 4,430,080 A † | 2/1984 | Pasquini |
| 5,609,584 A | 3/1997 | Gettig et al. |
| 6,500,153 B1 | 12/2002 | Sheppard et al. |

(Continued)

FOREIGN PATENT DOCUMENTS

| JP | 2014514051 A | 6/2014 |
| WO | 2012134513 A1 | 10/2012 |

(Continued)

OTHER PUBLICATIONS

PCT International Search Report and Written Opinion in PCT/US2017/055023 dated Dec. 19, 2017, 16 pages.

(Continued)

*Primary Examiner* — Jason E Flick
(74) *Attorney, Agent, or Firm* — Servilla Whitney LLC

(57) ABSTRACT

A syringe having barrel and a non-luer tip that is not connectable to an intravenous device is disclosed. The syringe as an enteral collar engagement feature adjacent the distal end of the syringe barrel. The syringe has an enteral collar having a distal end and proximal end, the proximal end having a syringe engagement feature complementary to and engagable with the enteral collar engagement feature. The enteral collar is sized to permit connection to an enteral device and prevent connection to a device having a luer connector

22 Claims, 11 Drawing Sheets

(56) References Cited

U.S. PATENT DOCUMENTS

| | | | |
|---|---|---|---|
| 6,599,269 B1 | 7/2003 | Lewandowski et al. | |
| 7,066,914 B2 | 6/2006 | Andersen | |
| 7,955,317 B2 | 6/2011 | Fournie | |
| 8,292,875 B2 | 10/2012 | Kennard | |
| D710,499 S | 8/2014 | Kawamura | |
| D711,530 S | 8/2014 | Gleason, Jr. et al. | |
| D714,935 S | 10/2014 | Nishioka | |
| 8,888,758 B2 | 11/2014 | Mansour et al. | |
| D765,837 S | 9/2016 | Lev et al. | |
| D767,124 S | 9/2016 | Lev et al. | |
| D785,162 S | 4/2017 | Swisher et al. | |
| D861,161 S | 9/2019 | Schuessler | |
| 2006/0047251 A1* | 3/2006 | Bickford Smith | A61M 39/10 604/240 |
| 2007/0076401 A1† | 4/2007 | Carrez | |
| 2008/0140020 A1 | 6/2008 | Shirley | |
| 2010/0022966 A1 | 1/2010 | Kennard | |
| 2011/0046568 A1 | 2/2011 | Enns et al. | |
| 2012/0022457 A1 | 1/2012 | Silver | |
| 2012/0078214 A1 | 3/2012 | Finke et al. | |
| 2012/0150129 A1 | 6/2012 | Jin | |
| 2013/0030379 A1 | 1/2013 | Ingram et al. | |
| 2013/0090606 A1 | 4/2013 | Shams | |
| 2013/0158560 A1 | 6/2013 | Gleason et al. | |
| 2013/0226100 A1 | 8/2013 | Lev | |
| 2013/0237904 A1 | 9/2013 | Deneburg et al. | |
| 2013/0270819 A1 | 10/2013 | Amborn et al. | |
| 2014/0228811 A1* | 8/2014 | Charles | A61M 39/14 604/513 |
| 2016/0106928 A1 | 4/2016 | Davis et al. | |
| 2016/0159635 A1 | 6/2016 | Davis et al. | |
| 2016/0279032 A1* | 9/2016 | Davis | A61J 7/0053 |

FOREIGN PATENT DOCUMENTS

| | | |
|---|---|---|
| WO | 2015146831 A1 | 10/2015 |
| WO | 2018067629 A1 | 4/2018 |
| WO | 2018067929 A1 | 4/2018 |

OTHER PUBLICATIONS

Non-Final Office Action in U.S. Appl. No. 29/695,580 dated Oct. 4, 2019, 8 pages.

Reducing the Risk of Medical Device Tubing Misconnections, ENFit Low Dose Tip Syringe Review, GEDSA, web page http://stayconnected.org/enfit-medical-guidelines/, 11 pages, published at least as early as May 1, 2016, retrieved from Internet Archive Wayback Machine https://web.archive.org/web/20160501084017/http://stayconnected.org/ on Sep. 25, 2018.†

* cited by examiner
† cited by third party

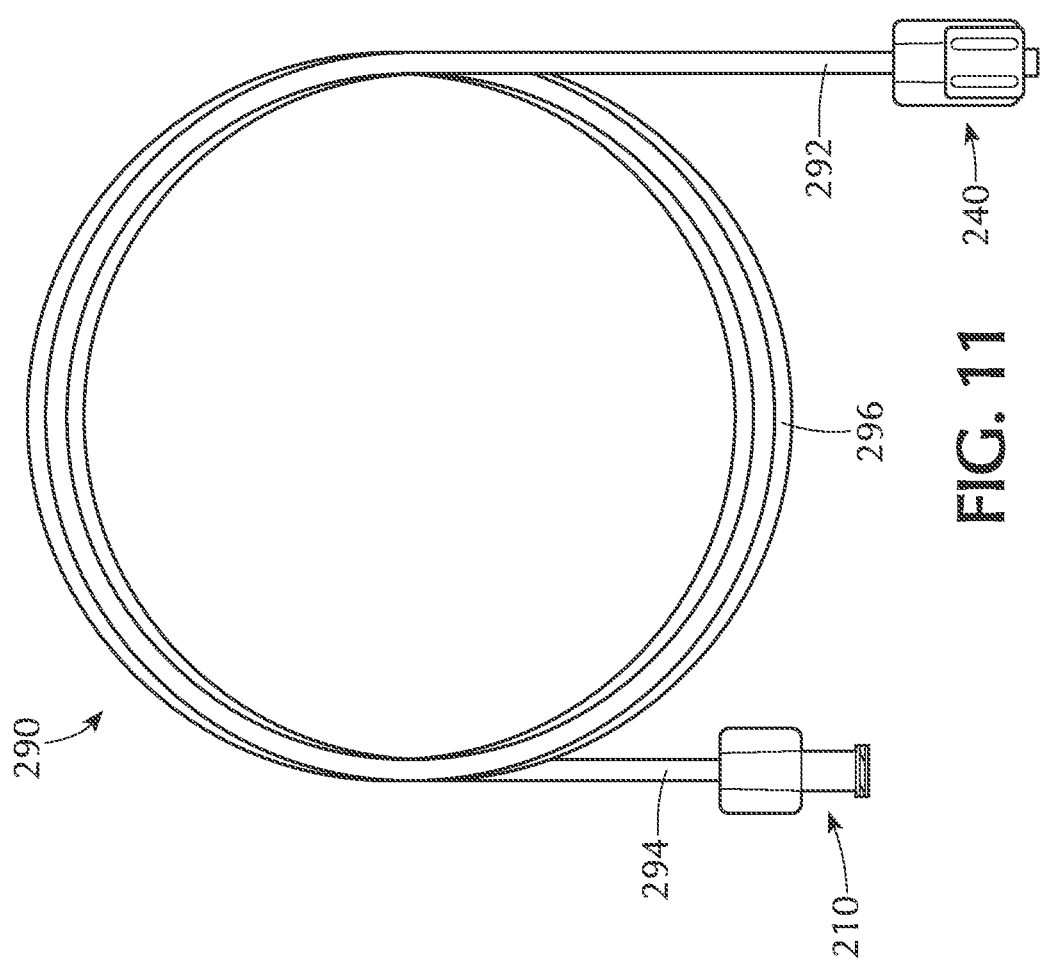

SYRINGE WITH ENTERAL CONNECTION FEATURE

TECHNICAL FIELD

Aspects of the present disclosure relate to a syringe with an enteral connection feature that prevents connection to non-enteral devices.

BACKGROUND

Enteral nutrition involves delivery of nutrient formula or medicine to the gastrointestinal tract. Administration of nutrients to a patient can be accomplished with an enteral feeding system, assembly or device. Enteral feeding systems typically utilize catheters inserted into a patient's nose or mouth, through which nutrients are administered to the gastrointestinal tract. A syringe or another device may be connected to the catheter to deliver the nutrients through the catheter. Nutrients and food may also be directly administered to a patient's mouth by a syringe, which may be referred to as an "oral syringe" or "oral delivery" of medication and does not require connection to a catheter or other device. Intravenous catheters are inserted into the vasculature of patients to effect intravascular treatment, which delivering medication through the circulatory or cardiovascular system by accessing any blood vessel. Such catheters catheters include intravenous (IV) catheters, which are inserted into veins, and intra-arterial catheters, which are inserted into arteries.

Syringes are used to deliver fluids for a variety of medical applications, including, for example, oral delivery of nutrients, storage and delivery of fluid to enteral systems by connecting the syringe to an enteral connection, and intravenous delivery of fluids or medication. Delivery of medication through intravenous syringes involves connecting the distal end of a syringe to a catheter by a luer connection. A standard male luer tip or standard male connector has specifications as provided by the International Organization for Standardization (ISO) defined in ISO 594-1:1986 and 594-2:1998, including a 6% taper that increases from the open distal end to the proximal end and an outer cross-sectional diameter at the distal end of the tip measuring between about 0.1545 inches (3.925 mm) and about 0.1570 inches (3.990 mm) for rigid material and between about 0.1545 inches (3.925 mm) and about 0.1585 inches (4.027 mm) for semi-rigid material. A standard female luer hub or standard female luer connector may have a 6% taper that decreases from the open proximal end to the distal end and an inner cross-sectional diameter at the open proximal end measuring between about 0.168 inches (4.270 mm) to about 0.170 inches (4.315 mm). In devices that have standard female luer connectors that incorporate tabs or lugs for connection to a corresponding male luer lock connector, the outer cross-sectional diameter of the standard female luer connector, including the lugs, is in the range from about 0.307 inches (7.80 mm) to about 0.308 inches (7.83 mm). In devices that have standard female luer connectors that do not incorporate tabs or lugs for connection to a corresponding male luer lock connector, the outer cross-sectional diameter may be about 0.224 inches (5.700 mm) for rigid connectors and about 0.265 inches (6.730 mm) for semi-rigid connectors, based on the maximum outside diameter of the standard female luer connector at the base of the lugs of ISO 594-2. The minimum length of the standard luer tip and/or the standard luer hub is 0.295 inches (7.500 mm), according to ISO 594-1. As used herein, the phrases "standard male luer connector," "standard male luer tip," "standard female luer hub" and "standard female luer connector" shall refer to connectors having the above dimensions.

Delivery of enteral fluid such as breast milk or formula from a syringe having a barrel and a plunger in the barrel is achieved by advancing the plunger into the barrel to pressurize the fluid within the barrel and discharge the fluid from the distal tip of the syringe. Oral dose syringes have a barrel with distal tip defining a channel having a diameter substantially larger than the diameter of a needle cannula. For a typical oral syringe, the distal tip defines a smooth exterior surface that is insertable into the mouth of a patient to orally introduce medication or other fluids into a patient.

Limiting the use of standard luer tips and connectors to use with vascular access systems is one consensus accepted by device manufacturers and regulatory bodies. For example, the recent adoption of ISO 80369-3 provides a uniform standard for small bore connectors for enteral applications. However, the adoption of ISO 830369-3 will result in a variety of syringe types to deliver fluids to patients intravenously, orally and enterally. It would be desirable to provide a syringe that could be used to connect to enteral systems having enteral connections meeting the ISO 80369-3 standard and also be used as on oral syringe, while preventing connection to standard luer tips and connectors.

SUMMARY

A first aspect of the present disclosure pertains to a syringe comprising a syringe barrel having a distal end, an open proximal end, a sidewall extending between the distal end to the open proximal end, the sidewall defining a chamber, and an enteral collar engagement feature adjacent the distal end of the syringe barrel; a non-luer tip dimensioned such that the non-luer tip is not connectable to an intravenous device, the non-luer tip defining a fluid pathway in fluid communication with the chamber; and an enteral collar having a distal end and a proximal end, the proximal end having a syringe engagement feature complementary to and engagable with the enteral collar engagement feature, the enteral collar surrounding the non-luer tip when the syringe engagement feature is engaged with the enteral collar engagement feature, and the enteral collar being sized to permit connection to an enteral device and prevent connection to a device having a luer connector.

A second aspect of the present disclosure pertains to a syringe comprising a syringe barrel having a distal end, an open proximal end, a sidewall extending between the distal end to the open proximal end, the sidewall defining a chamber, a distal extension wall extending from the distal end of the syringe barrel and an enteral collar engagement feature on the distal extension wall; a non-luer tip dimensioned such that the non-luer tip is not connectable to an intravenous device, the non-luer tip defining a fluid pathway in fluid communication with the chamber; and an enteral collar having a distal end and a proximal end, the proximal end having a syringe engagement feature complementary to and engagable with the enteral collar engagement feature, the enteral collar surrounding the non-luer tip when the syringe engagement feature is engaged with the enteral collar engagement feature, and the distal end of the collar includes an outwardly extending lug for engaging a threaded, non-luer connector, and the enteral collar sized to permit connection to an enteral device.

Another aspect of the present disclosure pertains to a syringe comprising a syringe barrel having a distal end, an open proximal end, a sidewall extending between the distal end to the open proximal end, the sidewall defining a chamber; a non-luer tip dimensioned such that the non-luer tip is not connectable to an intravenous device, the non-luer tip defining a fluid pathway in fluid communication with the chamber; a peripheral enteral collar engagement feature between the distal end of the syringe barrel and the non-luer tip; and an enteral collar having a distal end and a proximal end, the proximal end having a syringe engagement feature complementary to and engagable with the enteral collar engagement feature, the enteral collar surrounding the non-luer tip when the syringe engagement feature is engaged with the enteral collar engagement feature, and the enteral collar sized and including internal threads to permit a threaded connection to an enteral device.

BRIEF DESCRIPTION OF THE DRAWINGS

FIG. 11 is a view of a line set including tubing, which can be used for connection to a syringe according to one or more embodiments.

DETAILED DESCRIPTION

Figure 1:
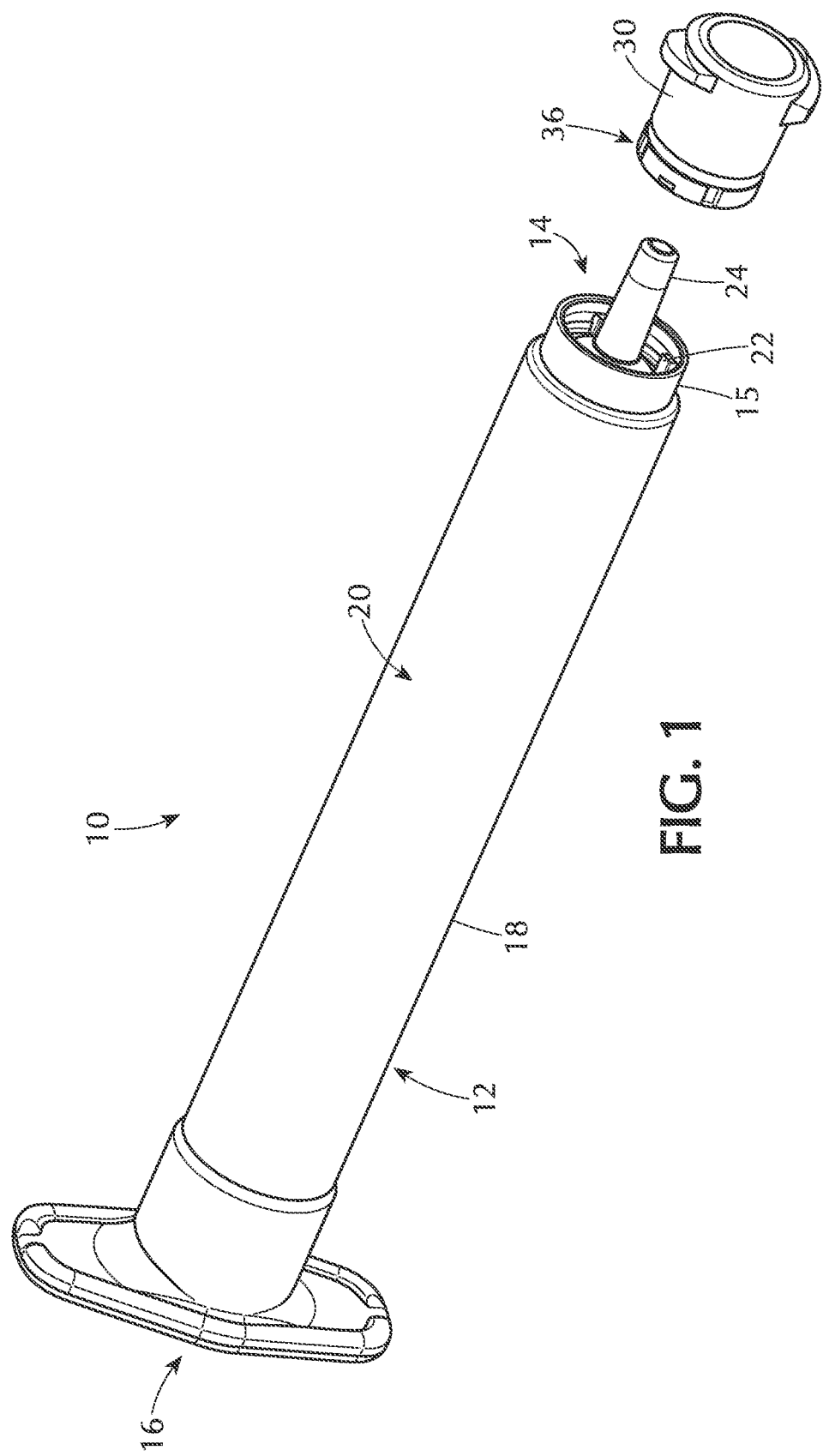
FIG. 1 is a perspective view of a syringe and collar according to one embodiment.
Figure 2:
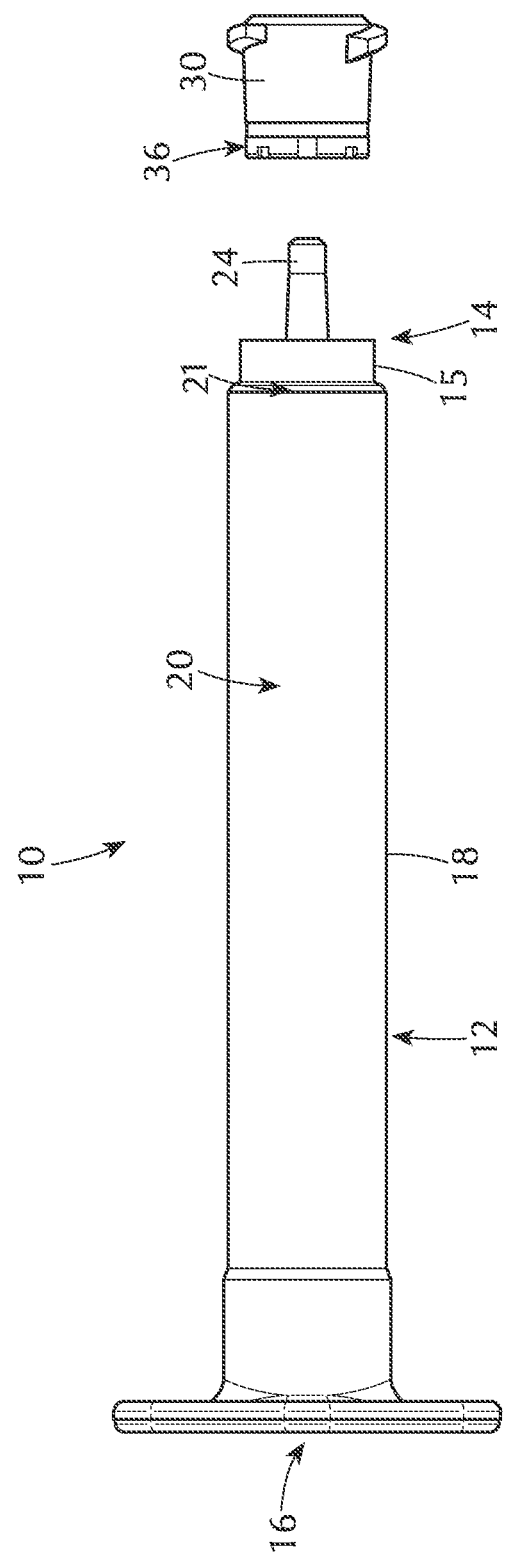
FIG. 2 is a side view of the syringe and collar shown in FIG. 1.

Before describing several exemplary embodiments of the disclosure, it is to be understood that the disclosure is not limited to the details of construction or process steps set forth in the following description. The disclosure is capable of other embodiments and of being practiced or being carried out in various ways.

In this disclosure, a convention is followed wherein the distal end of the device is the end closest to a patient and the proximal end of the device is the end away from the patient and closest to a practitioner.

The term "not connectable" with respect to male and female connectors refers to a connector having a shape, size, dimension or structure that prevents connection to another connector. For example, a female luer connector has a shape, size, dimension and/or structure that prevents it from forming a connection with a male non-luer connector and is thus not connectable with respect to the male non-luer connector. Such a female luer connector, however, has a shape, size, dimension and/or structure that permits formation of a connection with a male luer connector and is, thus, connectable with respect to the male luer connector. In another example, a female non-luer connector has a shape, size, dimension and/or structure that prevents formation of a connection with a male luer connector and is, thus, not connectable with respect to the male luer connector. Such a female non-luer connector has a shape, size dimension and/or structure that permits formation of a connection with a male non-luer connector and is thus connectable connector with respect to the male non-luer connector.

As used herein, the term "dimension" shall include the length, diameter or width of a geometric shape or the geometrically shaped components described herein. The term "cross-sectional diameter" shall include the measurement of the longest distance or greatest distance between two points on an edge of a cross-section of an object or component with a circular or non-circular cross-section. The two points may be located on the inside surface or outside surface of the edge of the cross-section of the object. The cross-sectional diameter of two points located on the inside surface of the edge of the cross-section of the object shall be referred to as the "inside cross-sectional diameter" and the cross-sectional diameter of two points located on the outside surface of the edge of the cross-section of an object shall be referred to as the "outside cross-sectional diameter." It should be recognized that "cross-sectional diameter" of objects having a circular cross-section may be referred to as the "cross-sectional dimension" or "diameter" of the object. The terms "cross-sectional dimension," "cross-sectional diameter" and "diameter" may be used interchangeably for objects having a circular cross-section.

One or more embodiments provide a syringe that has an enteral collar that will enable the syringe meet ISO 80369-3 misconnection requirements. In one or more embodiments, the syringe is a non-luer tapered oral syringe with features on the barrel to accept a collar that prevents connection to intravenous devices. In one or more embodiments, the features include either threads or snap/lock features which will allow an enteral collar to be placed and locked onto the syringe. In one or more embodiments, after the enteral collar is attached to the syringe, the collar will not translate or rotate, however, in other embodiments, the collar may translate or rotate. According to one or more embodiments, the syringe can be utilized to draw-up, fill and administer oral medication and fluids as normal oral syringes are currently used, and after the enteral collar is attached the syringe, it will be compliant to ISO 80369-3 and able to be utilized for enteral administration. The syringe according to one or more embodiments does not require any work flow changes in the pharmacy or at patient bed side to deliver oral medication. Thus, one or more embodiments provide a syringe that can be used for two functions, namely oral administration and enteral administration.

One or more embodiments provide a syringe that can be connected to enteral feeding sets and feeding tubes. In the industry, the connection is referred to as ENFit and is compliant to ISO 80369-3. According to one or more embodiments, a syringe is provided that permits the syringe to be connected to enteral tubing and enteral devices such as feeding bags and prevents connection to non-enteral devices, such as intravenous lines, urinary catheters and ventilator tubing. One or more embodiments provide a syringe that is compliant with ENFit devices and ISO 80369-3 and the syringe is not be compatible with a luer connection, thus preventing misadministration of an enteral feeding or medication by the wrong route. Thus, a syringe is provided that when a collar is attached, it has a connector has a unique enteral-specific design that provides a simple way to reduce the risk of enteral tube feeding misconnections and improve patient safety. Furthermore, after the collar is connected, the collar does not allow connectivity with any other connector for any other clinical use such as intravenous devices. According to one or more embodiments, a syringe is provided that when a collar is attached, provides an enteral-specific syringe that can be used to administer medicine, flush, hydrate, or bolus feed through the new ENFit feeding tubes and extension sets compliant with ISO 80369-3. One or more embodiments provide a syringe having a collar that does not connect with standard luer connectors that are compliant with ISO Standard 594/1 and 594/2. Thus, an embodiment of the disclosure provides a syringe having a connector with a dimension that is not compatible with standard sized intravenous connectors and ports to keep the two from being inadvertently coupled mechanically.

Aspects of the present disclosure pertain a syringe having an enteral collar with a male connector that prevents misconnection to other non-compatible female connectors. A male connector shall be defined herein as a male connector that has a shape, size, dimension or structure that differs from a non-compatible female connector. Non-compatible female connectors may include standard female luer connectors, which conform to ISO 594-1:1986 and 594-2:1998.

In one or more embodiments, non-compatible collars having female connectors may have a shape, size, dimension or structure that does not conform to ISO 594-1:1986 or ISO 594-2:1998. In such embodiments, the non-compatible female connector may have a shape, size, dimension or structure that prevents it from being characterized or defined as a female luer connector as defined above or according as ISO 594-1:1986 or ISO 594-2:1998. In one or more specific embodiments, non-compatible female connectors may have length and/or cross-sectional diameter that differs from a female luer connector as defined above or according ISO 594-1:1986 or ISO 594-2:1998. In a more specific embodiment, the non-compatible female connector may have a taper that differs from a luer connector as defined above or according ISO 594-1:1986 or ISO 594-2:1998. In an even more specific embodiment, the non-compatible female connector may have a more gentle taper (for example, 5% taper) than a female luer connector as defined above or according ISO 594-1:1986 or ISO 594-2:1998, a cross-sectional diameter that is smaller than a female luer connector as defined above or according ISO 594-1:1986 or ISO 594-2:1998 and/or a longer length than a female luer connector as defined above or according ISO 594-1:1986 or ISO 594-2:1998.

Referring now to FIGS. 1-5, a first embodiment of a syringe 10, which is shown as comprising a syringe barrel 12 having a distal end 14, an open proximal end 16, a sidewall 18 extending between the distal end 14 to the open proximal end 16, the sidewall 18 defining a chamber 20, and an enteral collar engagement feature 22 adjacent the distal end 14 of the syringe barrel 12. The syringe further includes a non-luer tip 24 dimensioned such that the non-luer tip 24 is not connectable to an intravenous device, the non-luer tip 24 defining a fluid pathway 26 in fluid communication with the chamber 20. The syringe further comprises an enteral collar 30 having a distal end 32 and a proximal end 34. The proximal end 34 of the enteral collar 30 has a syringe engagement feature 36 complementary to and engagable with the enteral collar engagement feature 22, the enteral collar 30 surrounding the non-luer tip 24 when the syringe engagement feature 36 is engaged with the enteral collar engagement feature 22. The enteral collar 30 is sized to permit connection to an enteral device and prevent connection to a device having a luer connector. In the embodiment shown, the non-luer tip 24 is at the distal end 14 of the syringe barrel 12 and the enteral collar engagement feature 22 is located between the open proximal end 16 and the distal end 14 of the syringe barrel.

Figure 4:
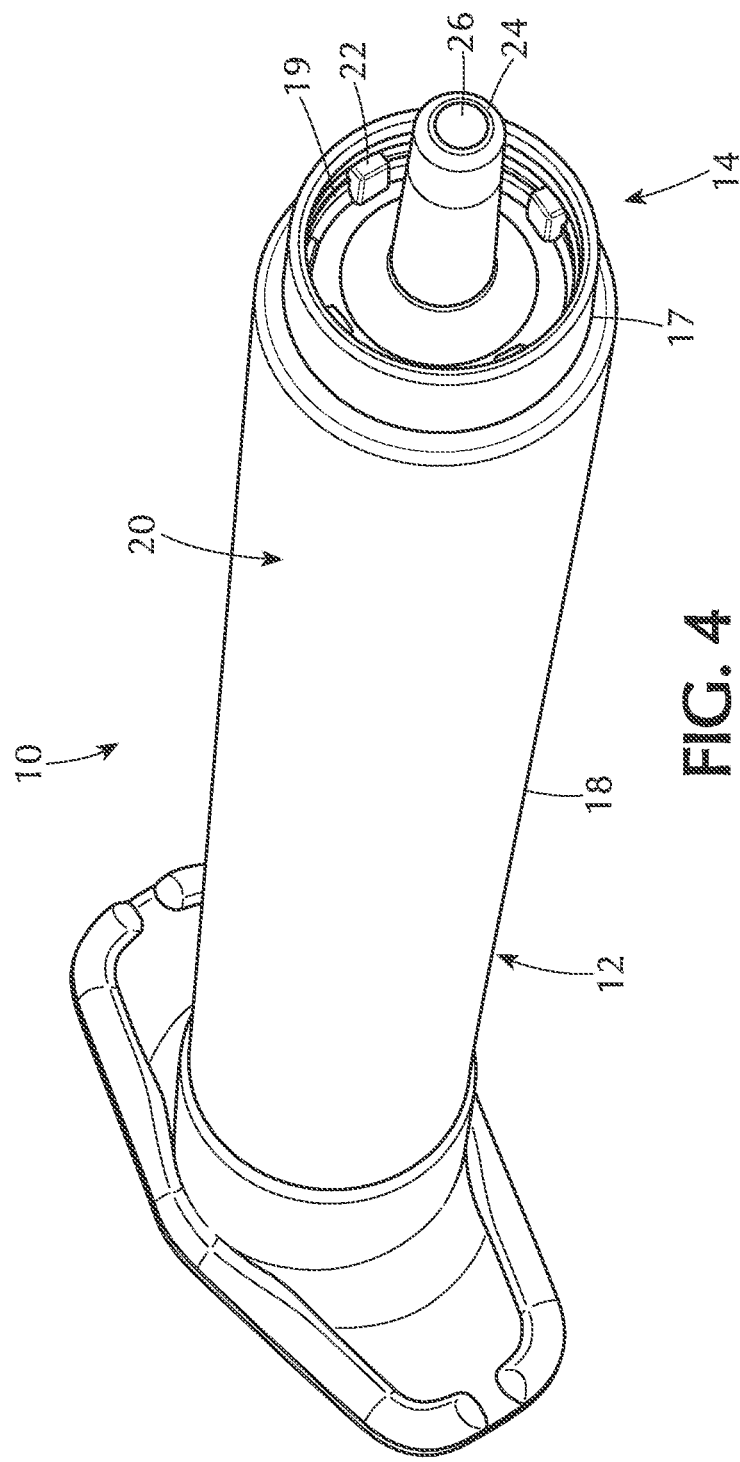
FIG. 4 is a distal end view of the syringe shown in FIG. 1.
Figure 5:
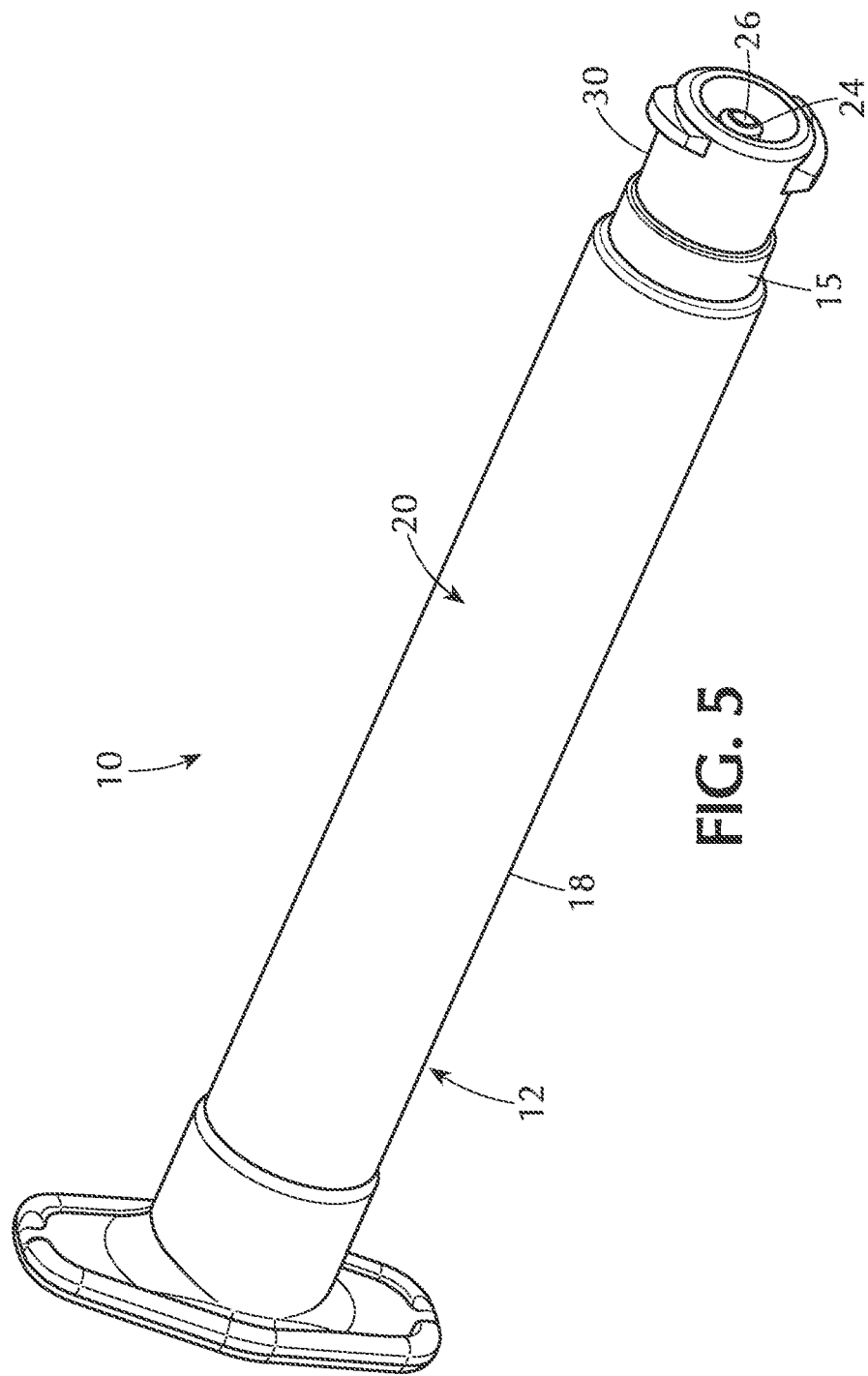
FIG. 5 is a perspective view of the syringe and collar shown in FIG. 1 with the collar connected to the syringe.
Figure 6:
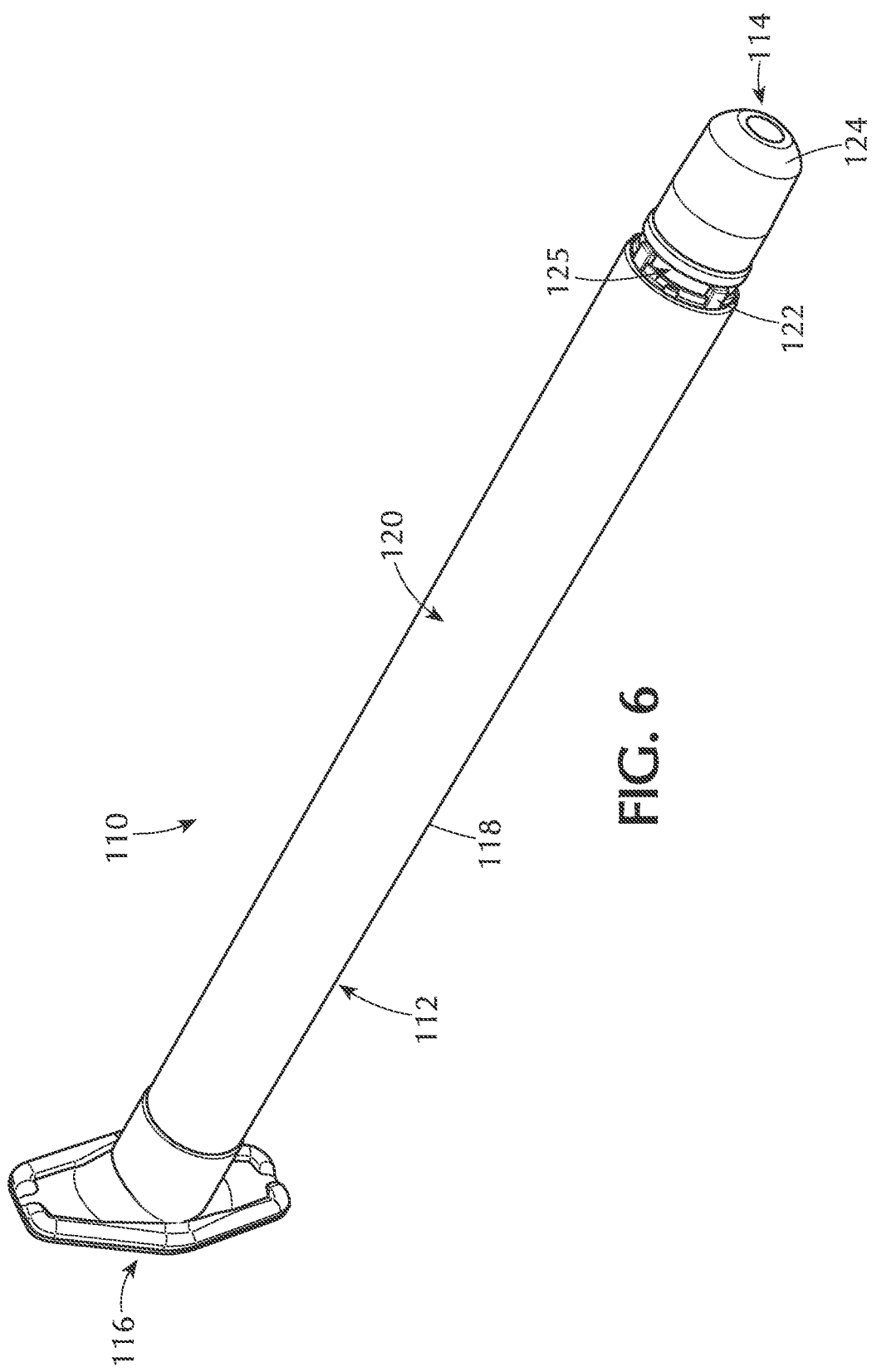
FIG. 6 is a perspective view of a syringe according to one embodiment.

As best shown in FIG. 5, in one or more embodiments, the enteral connection collar 30 is outside the fluid pathway 26 and not in fluid communication with the chamber 20. In other words, fluid contained in the chamber 20 of the syringe 10 flows through distal tip 24, and fluid flowing through the distal tip 24 is not in contact with the collar 30. In an embodiment, the enteral collar engagement feature 22 and the syringe engagement feature 36 includes complementary mating features selected from detents, tabs, fingers, slots, a snap-fitting, depressions and threads. In the embodiment shown as best shown in FIG. 3A and FIG. 4, the syringe engagement feature 36 is shown as a plurality of slots or depressions 37 on the proximal end 34 of the enteral collar 30, which engage enteral collar engagement feature 22 in the form of tabs on the distal end 14 of the barrel 12. This configuration could be reversed such that the depressions or slots are on the syringe and the tabs are on the collar. Alternatively, any type of complementary features that would allow the collar 30 to be snap fit to the syringe 10. Such complementary features could include fingers or detents or a threaded fitting between the collar 30 and the syringe 10. Thus, as shown in FIG. 3B the enteral collar engagement feature 36 can comprises collar threads 39 engagable with syringe threads (not shown) adjacent the distal end 14 of the syringe barrel 12.

In an embodiment, after engagement of the syringe engagement feature 36 and the enteral collar engagement feature 22, the enteral collar 30 is not removable from the syringe 10. In an embodiment, after engagement of the syringe engagement feature 36 and the enteral collar engagement feature 22, the enteral collar 30 is not rotatable with respect to the syringe 10. In the embodiment shown in FIGS. 1-5, the syringe barrel 12 distal end 14 includes a distal extension wall 15 including the enteral collar engagement feature 22. In one embodiment, and as best seen in FIG. 4, the distal extension wall 15 includes an interior surface 17 and an exterior surface 19, and the enteral collar engagement feature 36 is located on the interior surface 17.

Figure 3B:
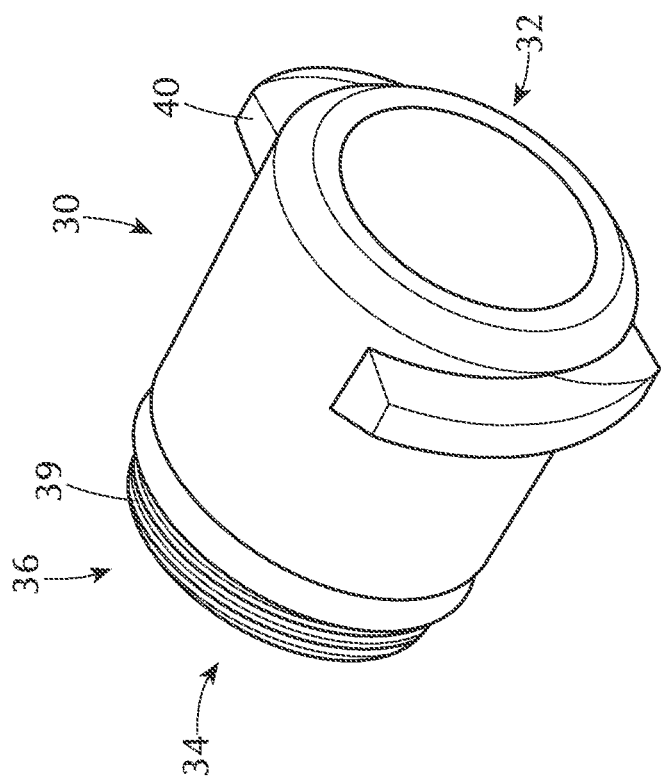
FIG. 3B is a perspective view of a collar according to one embodiment.
Figure 3A:
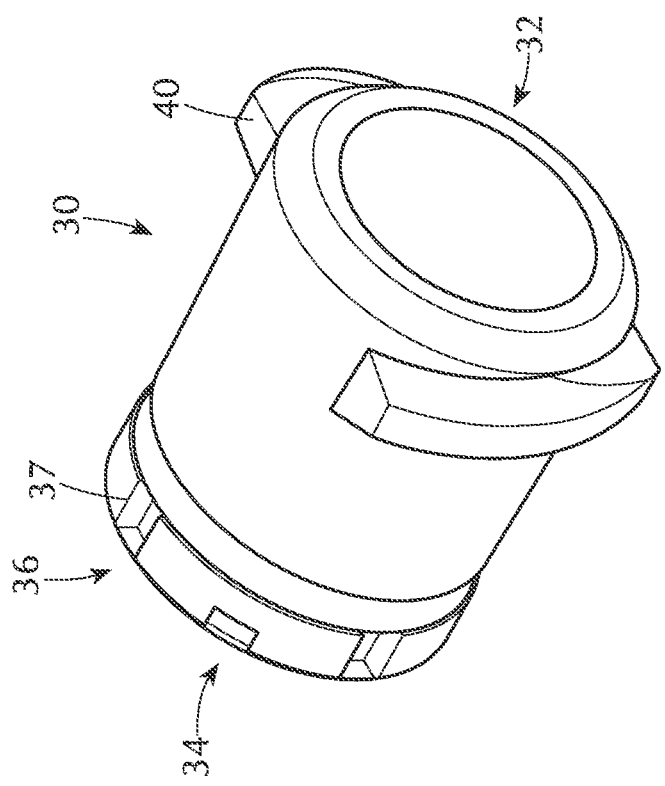
FIG. 3A is a perspective view of a collar according to one embodiment.

As shown in FIGS. 3A and 3B, the proximal end 34 of the enteral collar 30 includes the syringe engagement feature 36 and the distal end 32 of the enteral collar 30 includes a male thread or lug 40 extending outwardly for engaging a threaded, non-luer connector. In the embodiment shown, the enteral collar 30 includes a pair of male threads or lugs 40, which can engage female threads of a threaded non-luer connector. Any number of male threads or lugs 50 could be on the distal end 32 of the enteral collar 30. In specific embodiments, the enteral collar 30 having the male thread or lug 40 provides a male connector that provides an ENfit connection that conforms to ISO 80369-3 and is connectable with a female ENfit connector that conforms to ISO 80369-3.

Syringes usually retain some volume of medication in spaces within the chamber between the plunger and the distal end of the chamber, and these spaces are typically referred to as the "dead space" 21 of the syringe. In one or more embodiments, when the chamber 20 of the syringe 10 has a volume of less than 5 ml, and a dead space region that retains fluid in the chamber after fluid is expelled from the chamber, wherein the dead space region contains less than 0.07 ml of fluid. In one or more embodiments, a syringe 10 with a chamber 20 having a volume in a range of 5 ml and less than 10 ml has a dead space region less than or equal to 0.075 ml. In one or more embodiments, a syringe 10 with a chamber 20 having a volume of less than 20 ml and greater than 10 ml has a dead space region less than or equal to 0.10 ml.

Figure 7:
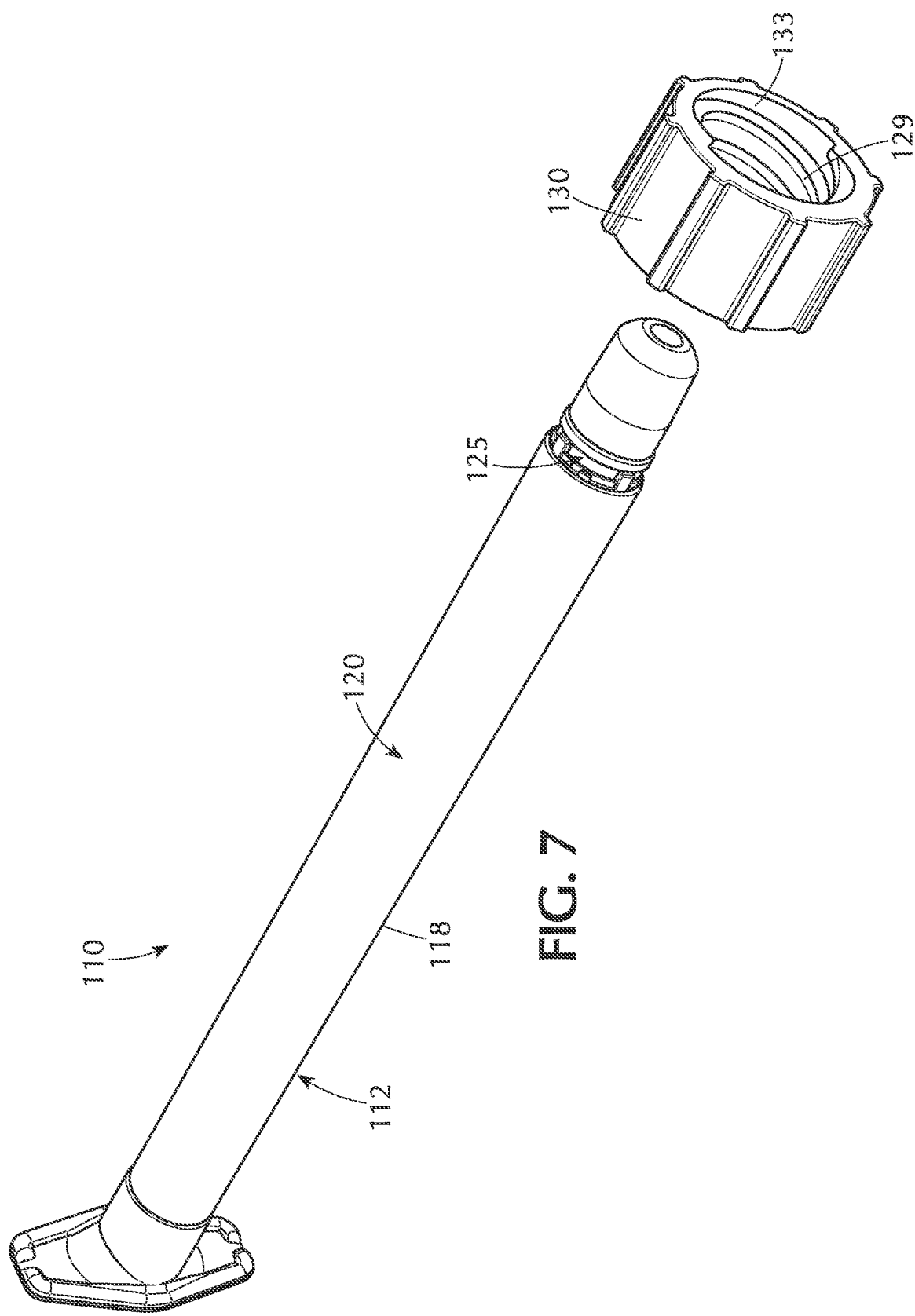
FIG. 7 is a perspective view of a syringe and collar according to one embodiment.
Figure 8:
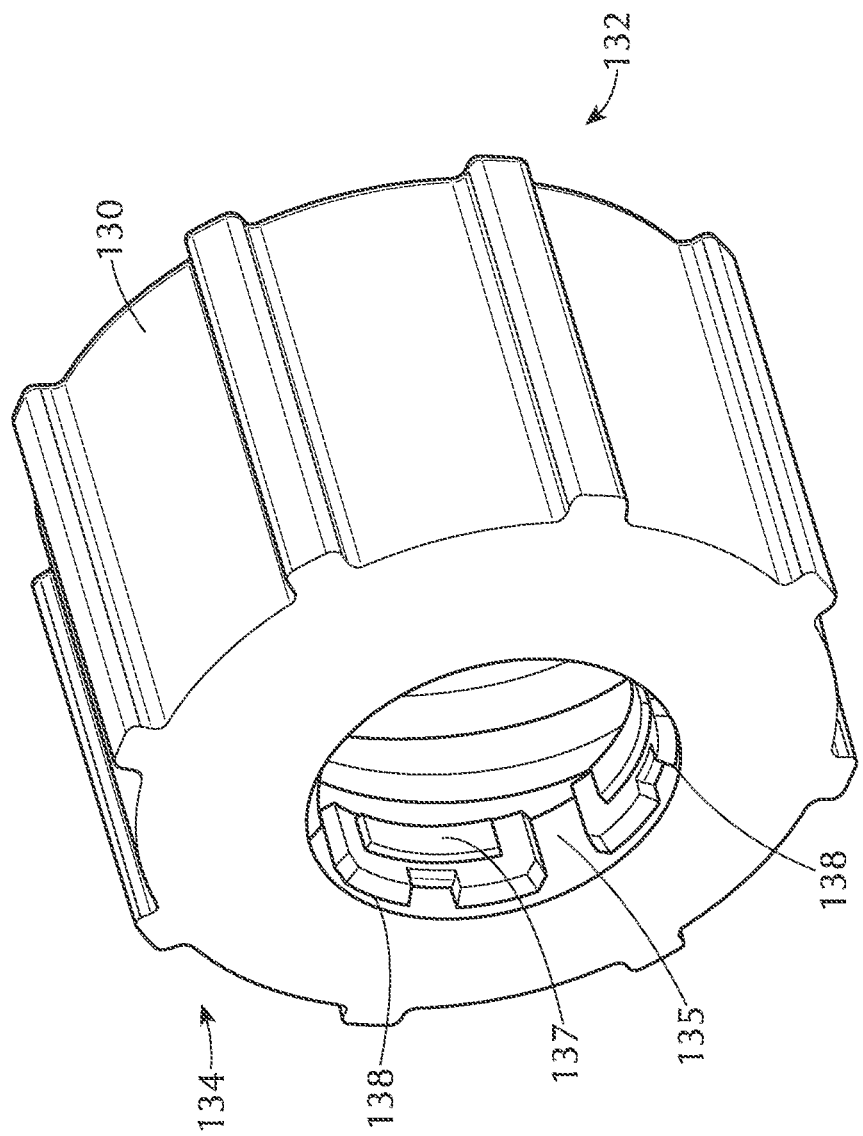
FIG. 8 is perspective view of the collar shown in FIG. 7.
Figure 9:
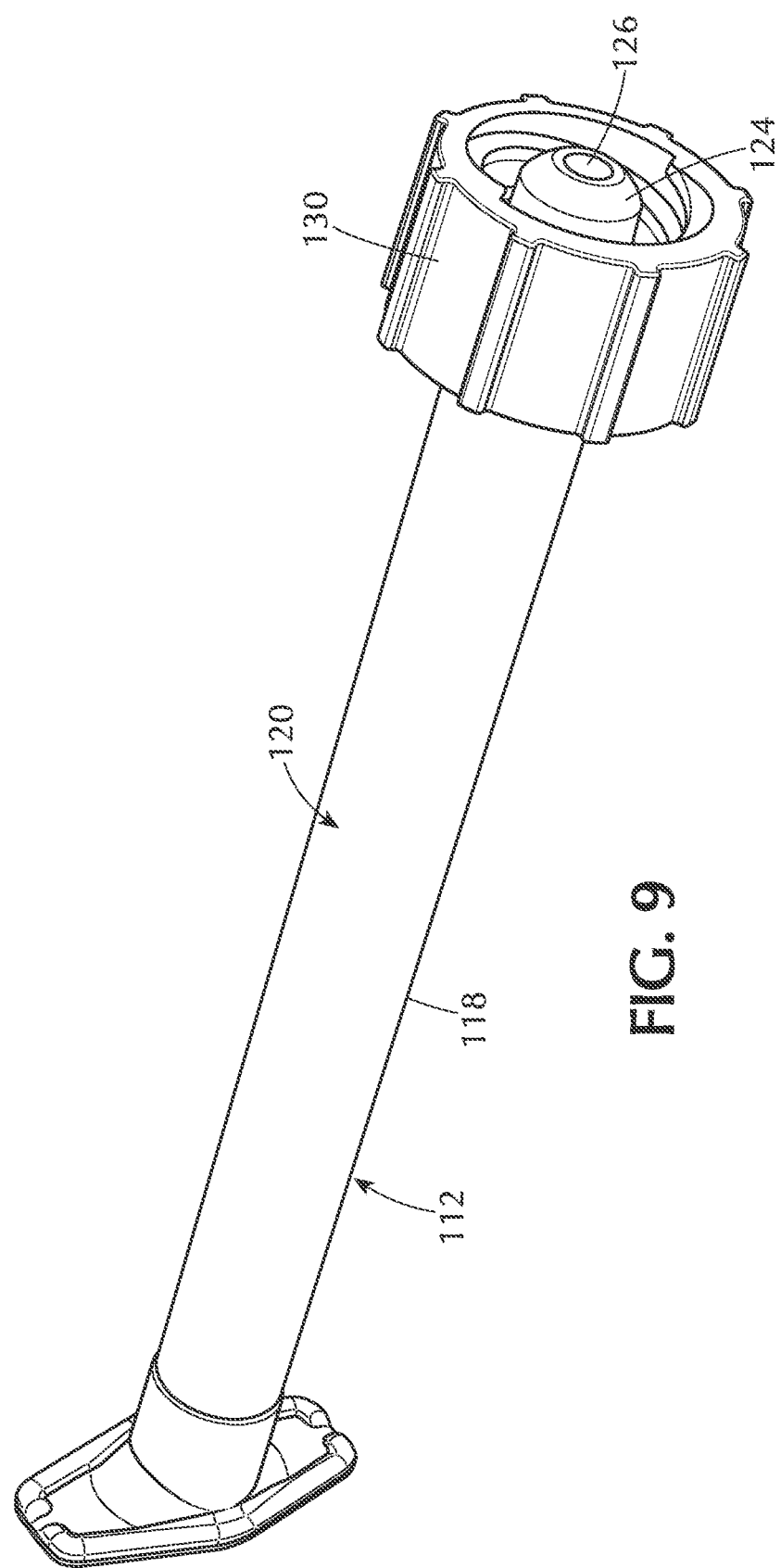
FIG. 9 is a perspective view of the syringe and collar shown in FIG. 7 with the collar connected to the syringe.
Figure 10:
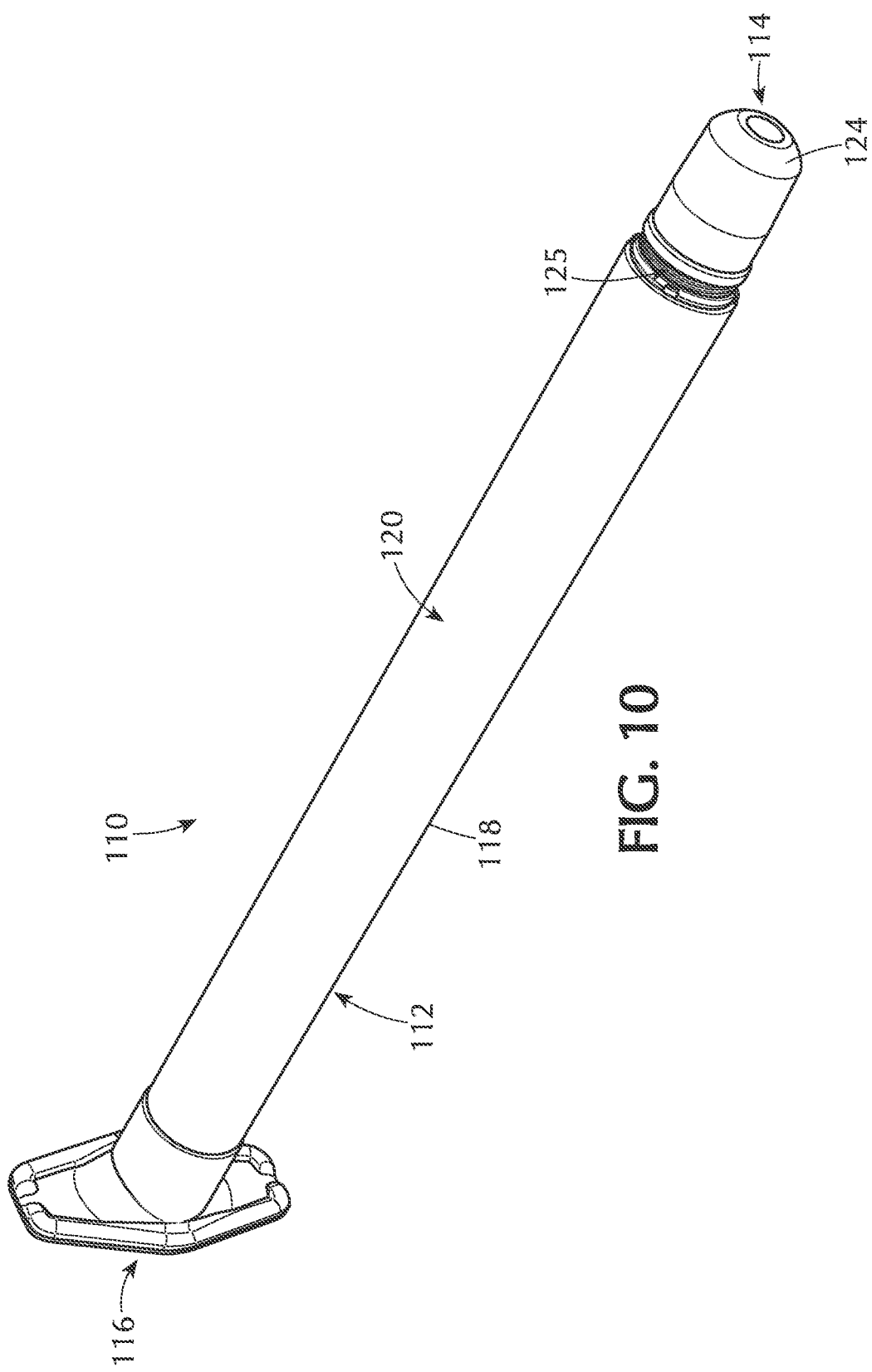
FIG. 10 is a perspective view of a syringe according to one embodiment.

Referring now to FIGS. 6-10, a second embodiment of a syringe 110 is shown. Similar to the syringe of the first embodiment, the syringe 110 includes a syringe barrel 112 having a distal end 114, an open proximal end 116, a sidewall 118 extending between the distal end 114 to the open proximal end 116, the sidewall 118 defining a chamber1 20, and an enteral collar engagement feature 122 adjacent the distal end 114 of the syringe barrel 112. The syringe further includes a non-luer tip 124 dimensioned such that the non-luer tip 124 is not connectable to an intravenous device, the non-luer tip1 24 defining a fluid pathway 126 in fluid communication with the chamber 120. The syringe further comprises an enteral collar 130 having a distal end 132 and a proximal end 134. The proximal end 134 of the enteral collar 130 has a syringe engagement feature 136 complementary to and engagable with the enteral collar engagement feature 122, the enteral collar 130 surrounding the non-luer tip 124 when the syringe engagement feature 136 is engaged with the enteral collar engagement feature 122. The enteral collar 130 is sized to permit connection to an enteral device and prevent connection to a device having a luer connector. In the embodiment shown, the non-luer tip 124 is at the distal end 114 of the syringe barrel 112 and the enteral collar engagement feature 122 is located in a peripheral depression 125 adjacent the distal end of the syringe barrel. In the second embodiment, the enteral collar engagement feature 122 is shown as projections or tabs 122 that engage complementary syringe engagement features 136, which is shown as channels 137 formed by ramped tabs 138. Ramped tabs 138 also provide gaps 135, which allow the collar 130 to be slidably mounted onto the distal end of the syringe 110 such that the projections or tabs 122 are positioned between the gaps 135. When the projections or tabs 122 are positioned between the gaps 135 and the enteral collar 130 is rotated with respect to the syringe 130, the projections or tabs 122 ride up the ramped tabs 138 on the collar 130 and become locked in the channels 137. The collar is not rotatable or removable after the collar 130 is locked to the syringe 110. In another embodiment shown in FIG. 10, the syringe 110 includes threads 131 that cooperate with threads on the proximal end of the enteral collar 130 (not shown), and a threaded connection can be made between the enteral collar 130 and the syringe 110. As best shown in FIG. 7, the enteral collar 130 in the second embodiment has an inner surface 133 with internal threads 129. The enteral collar 130 is outside the fluid pathway 126 and not in fluid communication with the chamber 120.

In the embodiment shown, the enteral collar 130 including the internal threads 129 provides a female non-luer connector, which can engage a male non-luer connector. In specific embodiments, the enteral collar 130 having the internal threads 129 provides a female connector that provides an ENfit connection that conforms to ISO 80369-3 and is connectable with a male ENfit connector that conforms to ISO 80369-3.

In one or more embodiments, the syringes described in this disclosure may be connected to a variety of enteral devices, for example, feeding bags and feeding catheters, which is typically accomplished by connecting the enteral collars described herein to flexible tubing. FIG. 11 shows an example of 290 tubing having a male adapter 240 and a female adapter 210 connected to an enteral feeding extension set 290. The male adapter 240 may be disposed at a distal end 292 and the female adapter 210 may be disposed at a proximal end 294. The enteral feeding extension set 290 comprises medical-grade flexible tubing 296. While the tubing 296 is shown coiled in FIG. 11, it will be appreciated that the flexible tubing may be uncoiled and extended the full length of the tubing 296. In use, the male adapter 240 can be connected to the enteral collar 130 having a female adapter coupled to the syringe 110. In another embodiment, the female adapter 210 can be connected the collar 30 of syringe 19 having a male adapter and luges or threads 40 to engage the female adapter. The components of the syringes including the enteral collars may be fabricated of a variety of materials suitable for medical and health care applications. For example, the female or male adapters may be fabricated from a medical-grade material, such as, but not limited to, nylon, polypropylene, polycarbonate, polyvinylidene fluoride, acrylonitrile butadiene styrene, and polyvinyl chloride.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A syringe comprising:
    a syringe barrel having a distal end, an open proximal end, a sidewall extending between the distal end to the open proximal end, the sidewall defining a chamber, and an enteral collar engagement feature adjacent the distal end of the syringe barrel;
    a non-luer tip dimensioned such that the non-luer tip is not connectable to an intravenous device, the non-luer tip defining a fluid pathway in fluid communication with the chamber; and
    an enteral collar having a distal end configured to make a threaded connection to an enteral device and a proximal end, the proximal end having a syringe engagement feature complementary to and engagable with the enteral collar engagement feature, the enteral collar surrounding the non-luer tip when the syringe engagement feature is engaged with the enteral collar engagement feature, and the enteral collar being sized to permit a threaded connection of the syringe to an enteral device and prevent connection to a device having a luer connector.

2. The syringe of claim 1, wherein the enteral collar is outside the fluid pathway.

3. The syringe of claim 1, wherein the enteral collar engagement feature and the syringe engagement feature comprise complementary mating features selected from detents, tabs, fingers, slots, a snap-fitting, depressions and threads.

4. The syringe of claim 1, wherein the syringe engagement feature comprises collar threads engagable with syringe threads adjacent the distal end of the syringe barrel.

5. The syringe of claim 1, wherein the syringe engagement feature and the enteral collar engagement feature engage via a snap-fitting.

6. The syringe of claim 1, wherein after engagement of the syringe engagement feature and the enteral collar engagement feature, the enteral collar is not removable from the syringe barrel.

7. The syringe of claim 1, wherein after engagement of the syringe engagement feature and the enteral collar engagement feature, the enteral collar is not rotatable with respect to the syringe barrel.

8. The syringe of claim 1, wherein the syringe barrel distal end includes an extension wall including the enteral collar engagement feature.

9. The syringe of claim 8, wherein the extension wall includes an interior surface and an exterior surface, and the enteral collar engagement feature is located on the interior surface.

10. The syringe of claim 8, wherein the proximal end of the enteral collar includes the syringe engagement feature and the distal end of the enteral collar includes a lug for engaging a threaded, non-luer connector.

11. The syringe of claim 10, wherein the chamber has a volume of less than 5 ml, and a dead space region that retains fluid in the chamber after fluid is expelled from the chamber, wherein the dead space region contains less than 0.07 ml of fluid.

12. The syringe of claim 1, wherein the non-luer tip is at the distal end of the syringe barrel and the enteral collar engagement feature is located between the open proximal end and the distal end of the syringe barrel.

13. The syringe of claim 12, wherein the enteral collar engagement feature is located in a peripheral depression adjacent the distal end of the syringe barrel.

14. The syringe of claim 12, wherein the enteral collar has an inner surface with threads.

15. The syringe of claim 10, wherein the collar is not removable or rotatable after the collar has been engaged with the enteral collar engagement feature.

16. The syringe of claim 12, wherein the chamber has a volume of less than 5 ml, and a dead space region that retains fluid in the chamber after fluid is expelled from the chamber, wherein the dead space region contains less than 0.07 ml of fluid.

17. A syringe comprising:
a syringe barrel having a distal end, an open proximal end, a sidewall extending between the distal end to the open proximal end, the sidewall defining a chamber, a distal extension wall extending from the distal end of the syringe barrel and an enteral collar engagement feature on the distal extension wall;
a non-luer tip dimensioned such that the non-luer tip is not connectable to an intravenous device, the non-luer tip defining a fluid pathway in fluid communication with the chamber; and
an enteral collar having a distal end configured to make a threaded connection to an enteral device and a proximal end, the proximal end having a syringe engagement feature complementary to and engagable with the enteral collar engagement feature, the enteral collar surrounding the non-luer tip when the syringe engagement feature is engaged with the enteral collar engagement feature, and the distal end of the collar includes an outwardly extending lug for engaging a threaded, non-luer connector, and the enteral collar sized to permit connection of the syringe to an enteral device.

18. The syringe of claim 17, wherein the chamber has a volume of 5 ml to less than 10 ml, and a dead space region that retains fluid in the chamber after fluid is expelled from the chamber, wherein the dead space region contains less than 0.075 ml of fluid.

19. The syringe of claim 17, wherein the enteral collar is outside the fluid pathway.

20. A syringe comprising:
a syringe barrel having a distal end, an open proximal end, a sidewall extending between the distal end to the open proximal end, the sidewall defining a chamber;
a non-luer tip dimensioned such that the non-luer tip is not connectable to an intravenous device, the non-luer tip defining a fluid pathway in fluid communication with the chamber;
a peripheral enteral collar engagement feature between the distal end of the syringe barrel and the non-luer tip; and
an enteral collar having a distal end and a proximal end, the proximal end having a syringe engagement feature complementary to and engagable with the enteral collar engagement feature, the enteral collar surrounding the non-luer tip when the syringe engagement feature is engaged with the enteral collar engagement feature, and the enteral collar sized and including internal threads to permit a threaded connection to an enteral device; wherein the enteral collar prevents connection to a device having a luer connector.

21. The syringe of claim 20, wherein the chamber has a volume in a range of 5 ml and less than 10 ml, and a dead space region that retains fluid in the chamber after fluid is expelled from the chamber, wherein the dead space region contains less than 0.075 ml of fluid.

22. The syringe of claim 20, wherein the enteral connection collar is outside the fluid pathway and not in fluid communication with the chamber.

* * * * *